US00PP24704P3

(12) United States Plant Patent
Los et al.

(10) Patent No.: US PP24,704 P3
(45) Date of Patent: Jul. 29, 2014

(54) ***MANDEVILLA* PLANT NAMED 'PATMANDEWI'**

(50) Latin Name: *Mandevilla sanderi*
Varietal Denomination: Patmandewi

(75) Inventors: Martijn Los, Klazienaveen (NL); Maurits van der Arend, Klazienaveen (NL)

(73) Assignee: Patio Plants V.O.F. (NL)

( * ) Notice: Subject to any disclaimer, the term of this patent is extended or adjusted under 35 U.S.C. 154(b) by 170 days.

(21) Appl. No.: 13/507,486

(22) Filed: Jul. 3, 2012

(65) Prior Publication Data

US 2014/0013475 P1 Jan. 9, 2014

(51) Int. Cl.
*A01H 5/00* (2006.01)

(52) U.S. Cl.
USPC ..... Plt./232

(58) Field of Classification Search
CPC ..... A01H 5/02
USPC ..... Plt./232
See application file for complete search history.

*Primary Examiner* — June Hwu
(74) *Attorney, Agent, or Firm* — Cassandra Bright

(57) ABSTRACT

A new and distinct *Mandevilla sanderi* cultivar named 'Patmandewi' is disclosed, characterized by white flowers. The new variety is a *Mandevilla,* typically produced as an outdoor ornamental plant.

2 Drawing Sheets

Latin name of the genus and species: *Mandevilla sanderi.*
Variety denomination: 'Patmandewi'.

BACKGROUND OF THE INVENTION

The new cultivar is the product of chance discovery. The new variety originated as a naturally occurring branch mutation of the unpatented 'Mamasun' variety of *Mandevilla sanderi.*

The new variety was discovered by the inventors, Martijn Los and Maurits van der Arend, both citizens of the Netherlands, on Dec. 1, 2009 in a commercial greenhouse belonging to the inventors in Klazienaveen, The Netherlands. After identifying the new variety as a potentially interesting selection, the inventors continued confidential testing and propagation of 'Patmandewi' assessing stability of the unique characteristics of this variety.

Asexual reproduction of the new cultivar 'Patmandewi' was first performed at the commercial greenhouse belonging to the inventors in Klazienaveen, The Netherlands by vegetative cuttings in early 2010. Access to all plants was restricted, as plants were kept in a greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'Patmandewi' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Patmandewi.' These characteristics in combination distinguish 'Patmandewi' as a new and distinct *Mandevilla* cultivar:

1. White flowers

PARENT COMPARISON

Plants of the new cultivar 'Patmandewi' are similar to the parent, *Mandevilla sanderi* 'Mamasun' in most horticultural characteristics. The new variety, however, produces a flower that lacks the darker colored floral tube striping of 'Mamasun'.

COMMERCIAL COMPARISON

Plants of the new cultivar 'Patmandewi' are similar to the commercial variety, *Mandevilla sanderi* 'Mamasun' in most horticultural characteristics. The new variety, however, produces a flower that lacks the darker colored floral tube striping of 'Mamasun'.

BRIEF DESCRIPTION OF THE PHOTOGRAPHS

Figure 1:
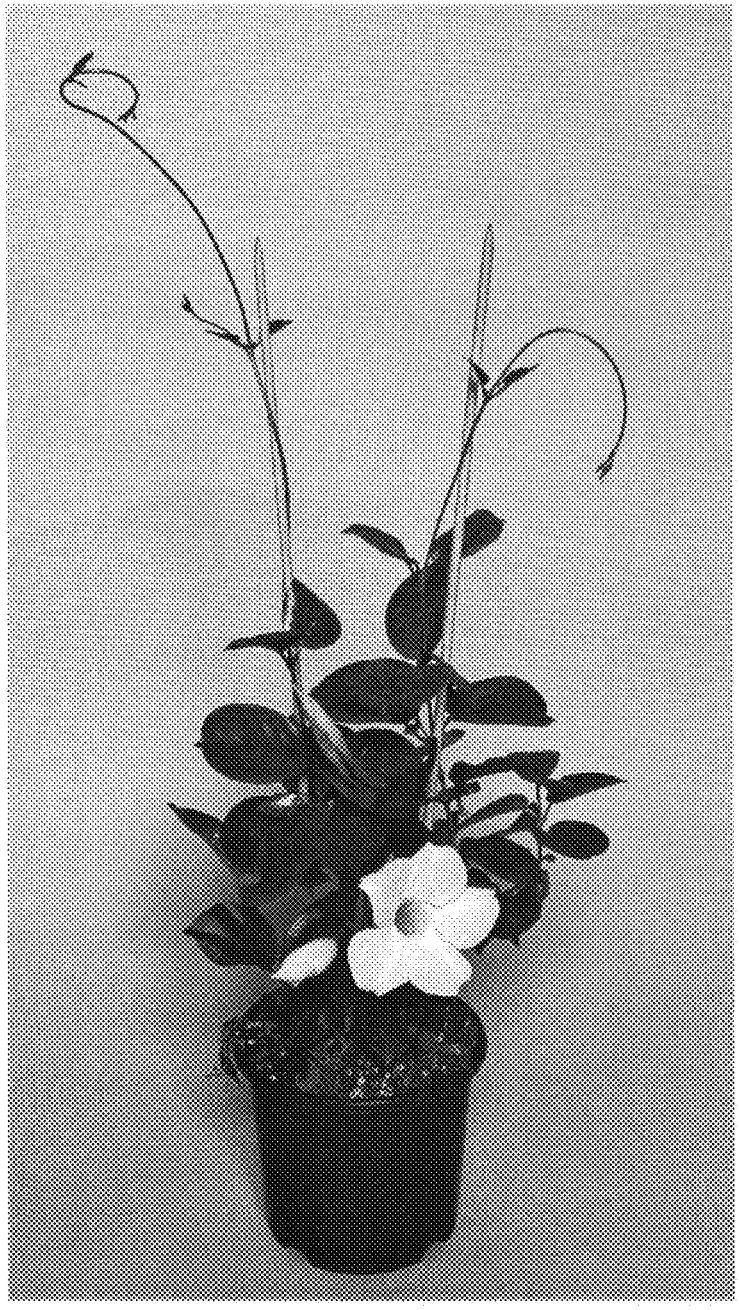

The accompanying photograph in FIG. 1 illustrates in full color a typical plant of 'Patmandewi' grown in a commercial greenhouse in Klazienaveen, The Netherlands. This plant is approximately 6-8 weeks old, shown planted in a 13 cm. container.

Figure 2:
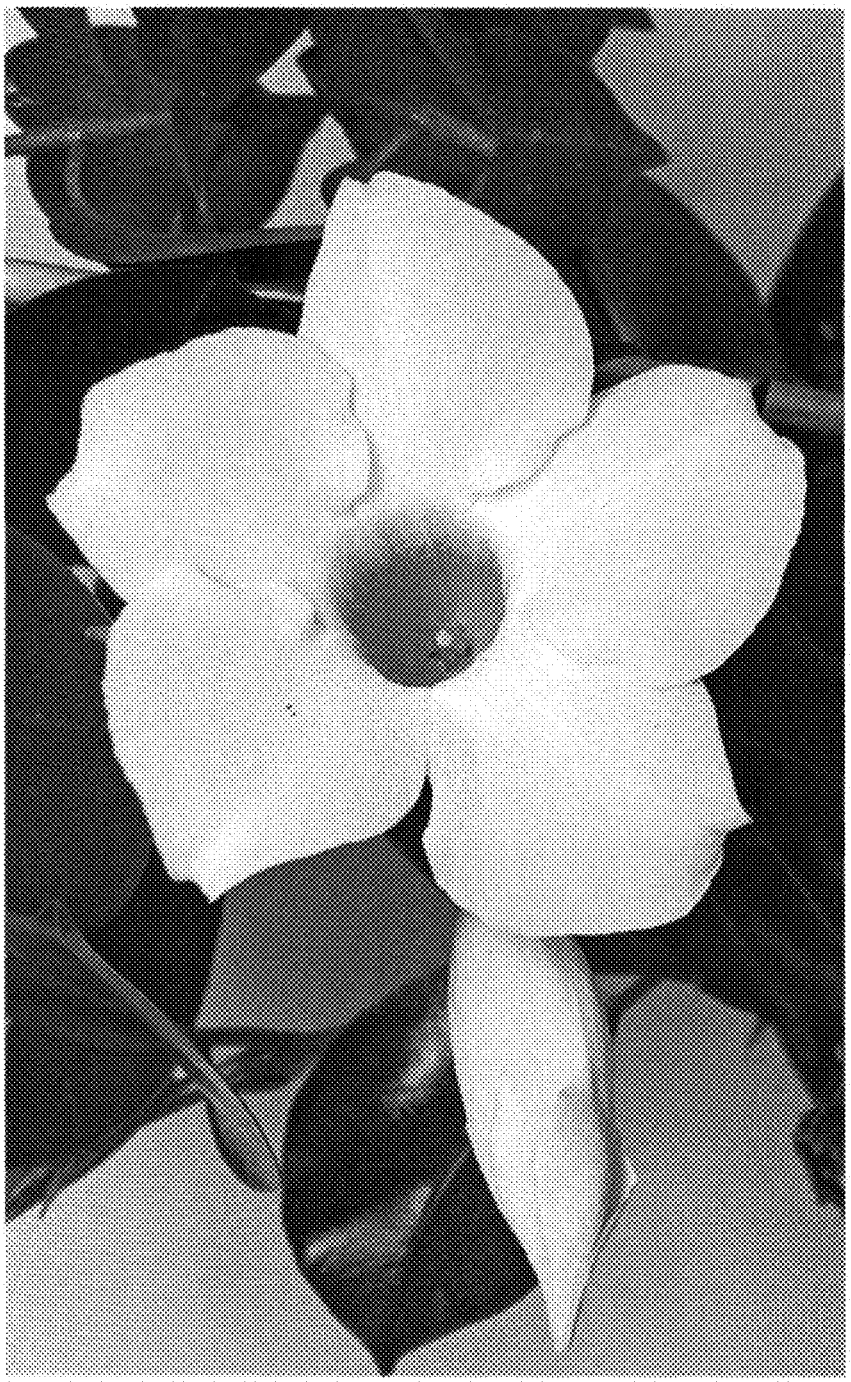

FIG. 2 illustrates in full color a close up of the flowers of 'Patmandewi.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'Patmandewi' plants grown in a greenhouse in Klazienaveen, The Netherlands. This was done in April 2012 from a plant 49 days old from a rooted cutting. Temperatures ranged from 16° C. at night to 20° C. during the day. No artificial light, photoperiodic treatments were given to the plants. No chemical treatments were given to the plants. Measurements and numerical values represent averages of typical plant types.
Botanical classification: *Mandevilla sanderi*.
Variety name: Patmandewi.
Variety denomination/filing name: 'Patmandewi'.

PROPAGATION

Time to initiate roots:
*Summer.*—14 to 21 days at approximately 16-20° C.
*Winter.*—14 to 21 days at approximately 16-20° C.
Root description: Moderately dense to dense, finely branched, non-fleshy, slightly fibrous, Colored RHS 156D Greyed-white.

PLANT

Growth habit: Twining.
Pot size of plant described: 13 cm circular.
Height: Average: 60.8 cm.
Plant spread: Average: 22.7 cm.
Growth rate: Moderately vigorous to vigorous.
Length of primary stem: Average: 56.4 cm.
Characteristics of main stem:
*Form.*—Rounded.
*Diameter.*—Average: 0.2 cm.
*Color.*—RHS 144A Yellow-green.
*Texture.*—Smooth, moderately glossy.
*Strength.*—Strong.
Branching characteristics: Moderately branching.
Quantity of primary lateral branches: Average: 4.
Length of primary lateral branches: 28.9 cm.
Characteristics of primary lateral branches:
*Form.*—Rounded.
*Diameter.*—Average: 0.15 cm.
*Color.*—RHS 144A Yellow-green.
*Texture.*—Smooth, moderately glossy.
*Strength.*—Strong.
Internode length: Average: 3.3 cm.

FOLIAGE

Leaf:
*Arrangement.*—Opposite.
*Quantity.*—Approximately 18 per branch (9 pairs).
*Average length.*—6.1 cm.
*Average width.*—4.1 cm.
*Shape of blade.*—Obovate.
*Apex.*—Abruptly acute.
*Base.*—Truncate to cordate.
*Margin.*—Entire.
*Texture of top surface.*—Smooth, glabrous, glossy.
*Pubescence.*—No leaf pubescence present.
*Aspect.*—Leaves in an average angle of 90° to lateral branches (=0°).
*Color.*—Young foliage upper side: RHS 152A Yellow-green. Slightly tinged RHS N199C Grey-brown. Young foliage under side: RHS 152A Yellow-green. Mature foliage upper side: RHS 139A and 147A Green and yellow-green but much darker. Mature foliage under side: RHS 146B to 147B Yellow-green.
*Venation.*—Type: Pinnate. Venation color upper side: RHS 143A Green. Venation color under side: RHS 144D Yellow-green.
*Petiole.*—Length: Average: 1.0 cm. Diameter: Average: 0.2 cm. Color: RHS 146A Yellow-green. Texture: Smooth, moderately glossy.

FLOWER

Natural flowering season: Spring, Summer and into autumn.
Inflorescence and flower type and habit: Auxiliary.
Rate of flower opening: Approximately 7 to 14 days from bud to fully opened flower.
Flower longevity on plant: Approximately 7 days.
Persistent or self-cleaning: Self-cleaning.
Bud:
*Shape.*—Narrow obovate.
*Length.*—Average: 3.9 cm.
*Diameter.*—Average: 0.6 cm.
*Color.*—RHS N144D Yellow-green, base colored RHS 143B Green, top strongly tinged RHS 185A Greyed-purple.
Flower size:
*Diameter.*—Average: 8.4 cm.
*Depth.*—Average: 8.2 cm. Throat Diameter: Average: 1.5 cm. Tube Length: Average: 5.2 cm. Tube Diameter at Base: Average: 0.4 cm.
Petals:
*Quantity.*—Average: 5.
*Arrangement.*—Campanulate. Petal Lobes: Length: Average: 4.0 cm. Width: Average: 3.0 cm. Shape: Unequal ovate.
*Apex.*—Broad unequal apiculate.
*Base.*—Broad cuneate, fused into the tube.
*Margin.*—Entire.
*Texture, outer surfaces.*—Petal Lobe: Smooth, slightly glossy, slightly velvety. Tube: Smooth, slightly glossy.
*Texture, inner surfaces.*—Petal Lobe: Smooth, slightly glossy, slightly velvety. Tube: Smooth, dull. Throat: Smooth, dull.
*Color.*—Outer Surfaces: Petal Lobe when opening: RHS 65C Red-purple. Tube when opening: RHS 150D Yellow-green. Petal Lobe fully opened: RHS N155B White. Tube fully opened: RHS 158D and 159C Orange-white. Petal Lobe fading: RHS 69D Red-purple. Tube fading: RHS N155C to N155D White. Inner Surfaces: Petal Lobe when opening: RHS 65C Red-purple. Tube when opening: RHS 15A Yellow-orange. Throat when opening: RHS N155B White. Petal Lobe fully opened: RHS 69D Red-purple. Tube fully opened: RHS 17B Yellow-orange. Throat fully opened: RHS NN155C White. Petal Lobe fading: RHS 69D Red-purple. Tube fading: RHS 16A Yellow-orange. Throat fading: RHS N155D White.
Sepals:
*Quantity.*—Average: 5.
*Arrangement.*—Rotate.
*Length.*—Average: 1.0 cm.
*Width.*—Average: 0.1 cm.
*Shape (overall).*—Linear. Apex: Narrow acute. Base: Broad cuneate.
*Margin.*—Entire.

*Color.*—Outer Surface: RHS 145A Yellow-green, tip colored RHS 180A to 180B Greyed-red. Inner Surface: Yellow-green; RHS 145C Yellow-green, base darker; RHS 145A Yellow-Green, tip colored RHS 180A Greyed-Red and 180B Greyed-red.

*Texture.*—Outer Surface: Smooth, slightly glossy. Inner Surface: Smooth, moderately glossy.

Peduncles:

*Length.*—Average: 6.7 cm.

*Diameter.*—Average: 0.2 cm.

*Angle.*—About 45° to the lateral branch.

*Strength.*—Strong.

*Texture.*—Smooth, glossy.

*Color.*—RHS 144A Yellow-green.

Pedicels:

*Length.*—Average: 1.4 cm.

*Diameter.*—Average: 0.25 cm.

*Angle.*—About 15° to the lateral branch.

*Strength.*—Strong.

*Texture.*—Smooth, moderately glossy.

*Color.*—RHS 144B Yellow-green.

Fragrance: Slightly fragrant.

REPRODUCTIVE ORGANS

Stamens:

*Number.*—Average: 5.

Anthers:

*Shape.*—Basifixed, double narrow oblong, tips touching thus forming a small cone of anthers.

*Length.*—Approximately 1.0 cm.

*Color.*—RHS 161D Greyed-yellow.

*Pollen.*—No pollen detected.

Pistil:

*Number.*—Average: 1.

*Length.*—Average: 2.5 cm.

*Style.*—Length: Average: 2.3 cm. Color: RHS 157A Green-white.

*Stigma.*—Shape: Sagittate. Color: RHS 151C Yellow-green. Ovary Color: RHS 143A Green.

OTHER CHARACTERISTICS

Seeds and fruits: No seeds/fruits detected to date.

Disease/pest resistance: Similar to other varieties of *Mandevilla.*

Temperature tolerance: Cold hardy to at least USDA zone 9.

What is claimed is:

1. A new and distinct cultivar of *Mandevilla sanderi* plant named 'Patmandewi' as herein illustrated and described.

* * * * *